United States Patent
Chang (10) Patent No.: US 7,955,300 B2
(45) Date of Patent: Jun. 7, 2011

(54) DISPOSABLE SAFETY SYRINGE WITH RETRACTABLE NEEDLE

(76) Inventor: Shu-Ming Chang, Nantou (TW)

(*) Notice: Subject to any disclaimer, the term of this patent is extended or adjusted under 35 U.S.C. 154(b) by 81 days.

(21) Appl. No.: 12/463,434

(22) Filed: May 11, 2009

(65) Prior Publication Data

US 2010/0286610 A1   Nov. 11, 2010

(51) Int. Cl.
*A61M 5/00* (2006.01)
(52) U.S. Cl. .......................................... 604/110
(58) Field of Classification Search .................... 604/110
See application file for complete search history.

(56) References Cited

U.S. PATENT DOCUMENTS

| | | | | |
|---|---|---|---|---|
| 2004/0236283 A1* | 11/2004 | Tang | ............................. | 604/197 |
| 2005/0049554 A1* | 3/2005 | Chueh | ........................... | 604/110 |
| 2005/0054979 A1* | 3/2005 | Liu | ............................... | 604/110 |
| 2005/0240150 A1* | 10/2005 | Gordon | ........................ | 604/110 |
| 2006/0189935 A1* | 8/2006 | Janek et al. | .................. | 604/110 |
| 2007/0043322 A1* | 2/2007 | Lee et al. | ...................... | 604/110 |
| 2007/0060885 A1* | 3/2007 | Wu | ............................... | 604/110 |
| 2007/0299395 A1* | 12/2007 | Pelkey et al. | ................. | 604/110 |
| 2008/0281266 A1* | 11/2008 | Walton et al. | ................. | 604/110 |
| 2009/0171285 A1* | 7/2009 | Wang | ............................ | 604/110 |
| 2009/0216188 A1* | 8/2009 | Woehr et al. | .................. | 604/110 |
| 2009/0312703 A1* | 12/2009 | Pickhard | ....................... | 604/110 |
| 2010/0063443 A1* | 3/2010 | Lin Lee | ....................... | 604/110 |

* cited by examiner

Primary Examiner — Nicholas D Lucchesi
Assistant Examiner — Diva Ranade (57) ABSTRACT

A disposable safety syringe in one embodiment includes a stepped syringe barrel comprising two opposite mating members on an inner surface proximate a distal end; a plunger comprising a connection member and a breakable section behind the connection member; a first needle assembly comprising a needle and a needle hub secured to the distal end of the syringe barrel; and a hollow second needle assembly shaped to lockingly secure to the first needle assembly in the syringe barrel, the second needle assembly comprising two opposite corresponding mating members on an outer surface, the corresponding mating members being lockingly engaged with the mating members. After dispensing, the plunger may clockwise rotate about the syringe barrel until the mating members and the corresponding mating members are unlocked lengthwise each other. The plunger, the second needle assembly, and the first needle assembly may move rearward to retract the needle within the syringe barrel.

3 Claims, 12 Drawing Sheets

DISPOSABLE SAFETY SYRINGE WITH RETRACTABLE NEEDLE

BACKGROUND OF THE INVENTION

1. Field of Invention

The invention relates to medical instruments and more particularly to a disposable, safe medical syringe with a retractable needle.

2. Description of Related Art

Special attention should be given to syringe needles because they are sharp enough to cause needle stick injuries before and after use. In particular, if a user is accidentally injured by a blood-stained needle, serious infections might be caused through the needle. Hence, safe medical syringes with retractable needles have been invented and some are commercially available.

For example, U.S. Pat. No. 7,276,049 discloses a disposable safety syringe designed to prevent syringe handlers from being pricked by a needle by covering the needle with a needle shield. The needle is covered with the needle shield after use. The needle shield is fitted over a syringe cylinder. A stopping tab prevents the needle shield from sliding off the cylinder. Inserting tabs are formed by cutting part of shield walls, and locking grooves are formed in the end of the inserting tabs. A fixing adapter has an engagement member formed in the inner side thereof and a number of elastic fins in the outer side thereof, which is fitted on the locking tab of the needle fixer.

Further, U.S. Pat. No. 7,393,340 discloses a disposable safety syringe including an automatically retractable needle. The syringe includes an automatically retractable needle for preventing said syringe from being reused, a cylindrical body defining, at one end thereof, a needle coupling end-piece and being opened at the other end portion thereof for introducing thereinto a piston having a scaling gasket. The patent is characterized in that on the piston are provided engaging means for engaging and retracting the needle after the delivering of the injection liquid.

Furthermore, U.S. Pat. No. 7,410,478 discloses a safety syringe with a needle retracting mechanism. The safety syringe includes a flexible holder-supporting seat that is sleeved around and that clamps a needle holder within a front end portion of a syringe barrel. A flexible sealing member seals an open front end of a plunger so as to define a vacuuming chamber in the plunger. When the plunger moves within the barrel to a front limit position, a holder-retaining front portion of the sealing member engages and retains the needle holder thereon. The plunger pushes the holder-supporting seat to separate from the needle holder such that the sealing member and the needle holder mover rearward within the syringe barrel due to negative pressure produced in the plunger, thereby retracting a needle into the syringe barrel.

Thus, the need for improvement still exists.

SUMMARY OF THE INVENTION

It is therefore one object of the invention to provide a disposable safety syringe with a retractable needle.

The above and other objects, features and advantages of the invention will become apparent from the following detailed description taken with the accompanying drawings.

DETAILED DESCRIPTION OF THE INVENTION

Referring to FIGS. 1 to 7, a disposable safety syringe in accordance with a first preferred embodiment of the invention comprises the following components as discussed in detail below.

Figure 1:
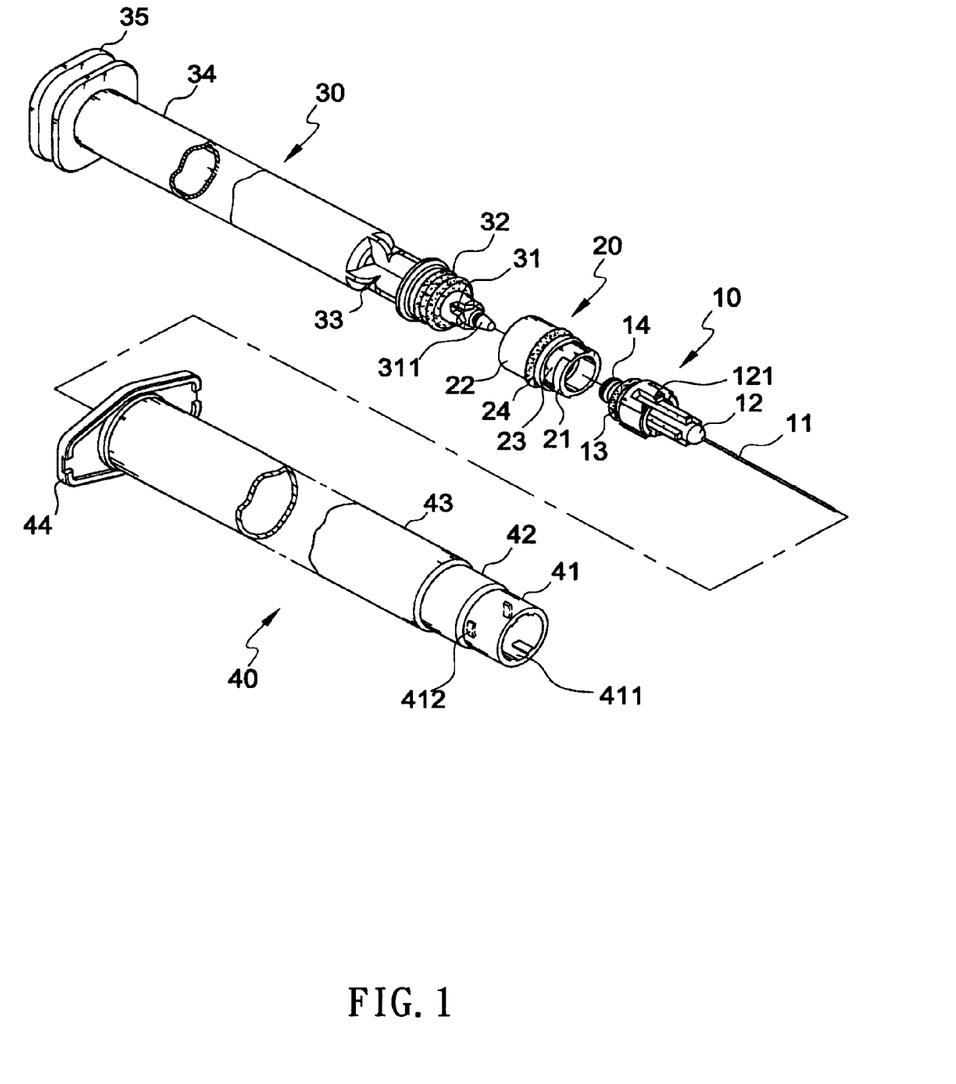
FIG. 1 is an exploded view of a first preferred embodiment of disposable safety syringe according to the invention.
Figure 2:
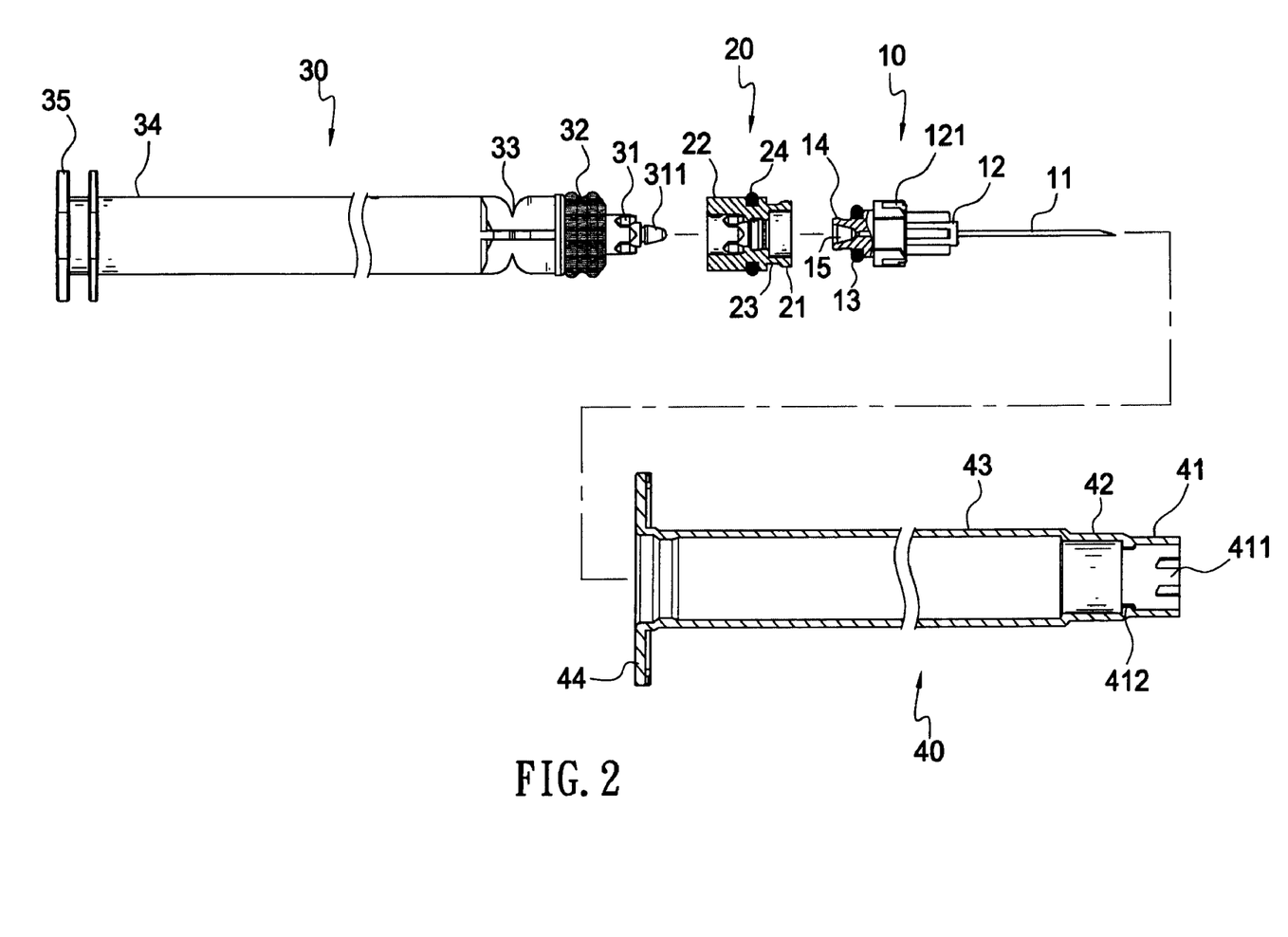
FIG. 2 is a longitudinal sectional view of the syringe of FIG. 1.
Figure 3:
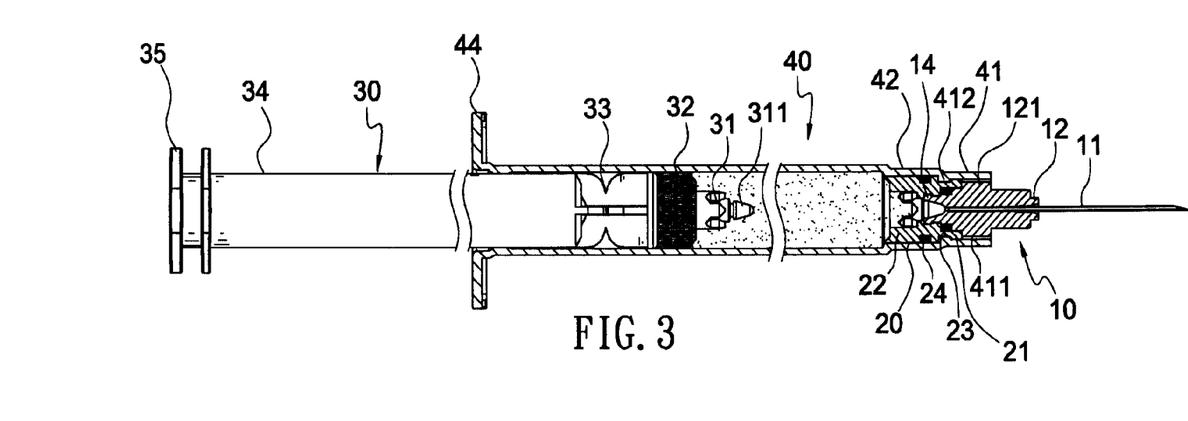
FIG. 3 is a longitudinal sectional view of the assembled syringe of FIG. 1 where the syringe barrel is filled with injection liquid prior to dispensing.
Figure 4:
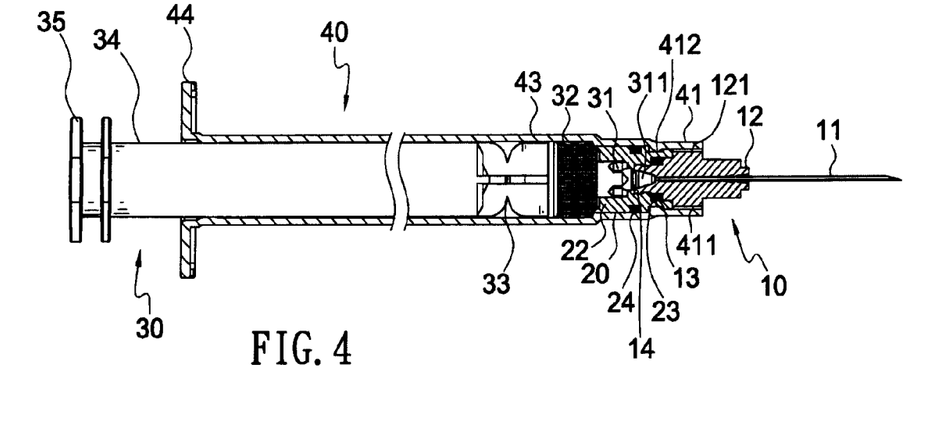
FIG. 4 is a view similar to FIG. 3 where the plunger is being pushed to dispense the injection liquid until the connection member is engaged with the first needle assembly in the second needle assembly.
Figure 5:
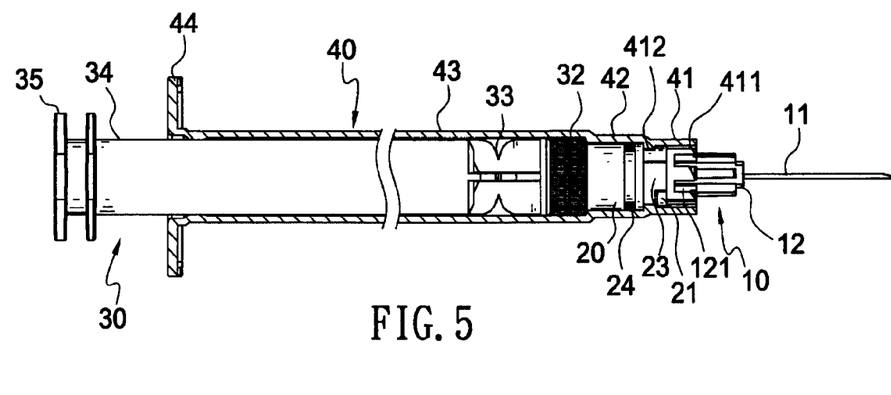
FIG. 5 is a cut-away side elevation view of FIG. 4 showing the plunger having not rotated after the dispensing.
Figure 6:
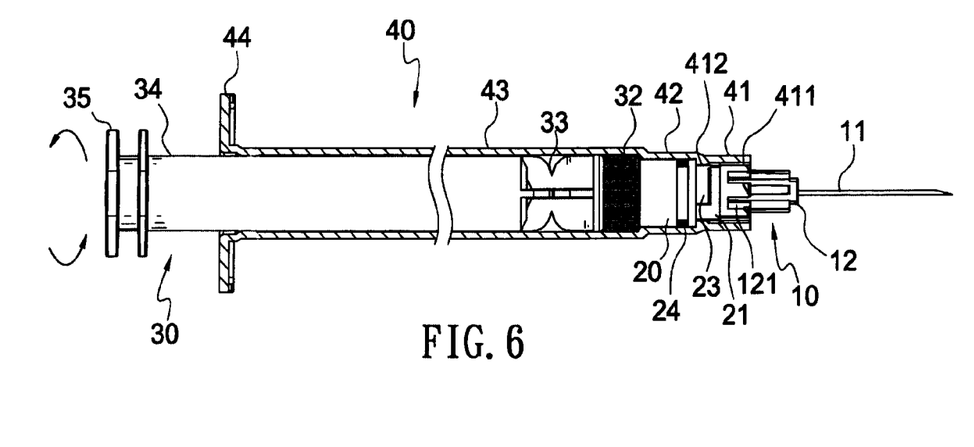
FIG. 6 is a view similar to FIG. 5 showing the plunger has rotated until bending points of the L-shaped grooves are stopped by the tabs so that a subsequent rearward movement of the plunger, the second needle assembly, and the first needle assembly can be effected.
Figure 7:
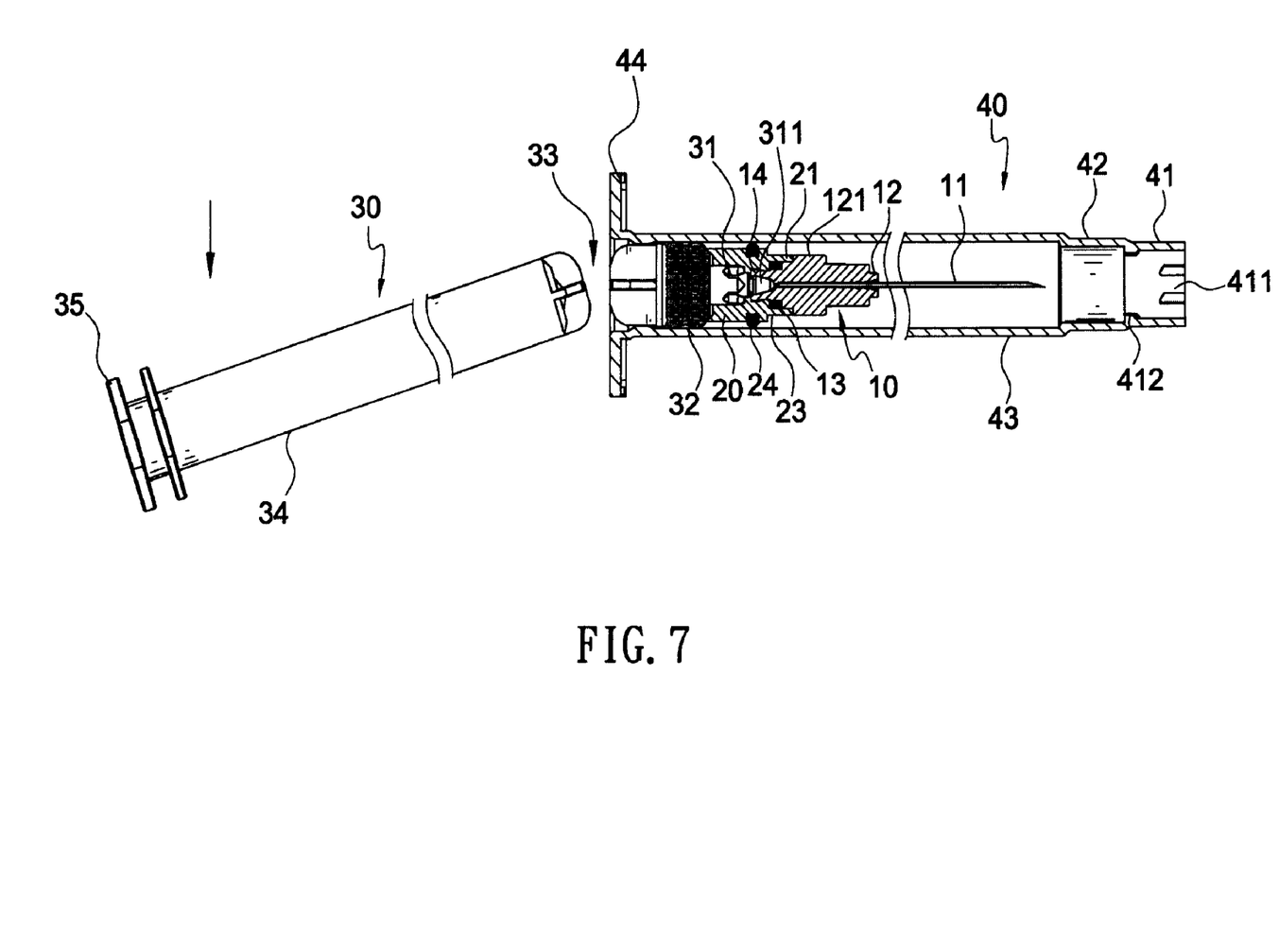
FIG. 7 is a view similar to FIG. 3 showing the breakable section of the plunger is broken by force after retracting the first needle assembly into the syringe barrel as a next step of FIG. 6.

A syringe barrel 40 is a stepped member and comprises, from front to rear, a first section 41 having a opposite internal lengthwise troughs 411 arranged around and proximate the mouth, two opposite tab 412 on the inner surface disposed rearward of the troughs 411, a second section 42 having inner and outer diameters larger than both of the first section 41, a third section 43 having inner and outer diameters larger than both of the second section 42, and an annular flange 44.

A plunger 30 comprises, from front to rear, a connection member 31 having a front cone 311, a sealing section 32, a breakable section 33, a main section 34, and two spaced rectangular flanges (i.e., handle) 35.

A first needle assembly 10 comprises, from front to rear, a needle 11, a cylindrical needle seat 12 having ridges 121 spaced therearound, an O-ring 13, and an extension 14. The needle 11 is disposed at one end of the first needle assembly 10, and the extension 14 is disposed at the other end. And the extension 14 includes a holding space 15. The ridges 121 are secured to the distal end of the syringe barrel 40.

A second needle assembly 20 is a hollow cylindrical member with a central bore shaped to sealingly secure to both the first needle assembly 10 (i.e., O-ring 13 and extension 14) and the plunger 30 (i.e., connection member 31). The second needle assembly 20 comprises, from front to rear, a first coupling section 21 having two opposite L-shaped grooves 23 formed on an outer surface, an O-ring 24, and a second coupling section 22. The first coupling section 21 is disposed at one end for covering the extension 14 of the first needle assembly 10. The second coupling section 22 is disposed inside the other end. The connection member 31 of the plunger 30 is inserting in the second needle assembly 20 and engaging with the second coupling section 22. The cone 311 of the connection member 31 is fully coupling in the first needle assembly 10.

The second needle assembly 20 has a portion locking fastened in the first section 41 by engaging the circumferential portions of the L-shaped grooves 23 with the tabs 412, and the remaining portion disposed in the second section 42. The first needle assembly 10 is releasably fastened in the first section 41 with its rear extension 14 and O-ring 13 being tightly secured to the second needle assembly 20, the ridges 121 and the troughs 411 matingly engaged each other, and the needle 11 exposed.

Liquid injection operation of the invention will be described below. First, the plunger 30 is pushed into the syringe barrel 40 until a predetermined position is reached with the cone 311 not entering the second needle assembly 20 (i.e., the plunger 30 being unlocked). Next, insert the needle 11 into a bottle of medical liquid. Next, pull the plunger 30 to create a vacuum in the syringe barrel 40 so that the liquid can be drawn into the syringe barrel 40. Stop the pulling if the syringe barrel 40 is filled with injection liquid. Next, remove the needle 11 from the bottle of medical liquid. Next, slightly push the plunger 30 to expel air from the syringe barrel 40 until the syringe barrel 40 is filled with a desired amount of medical liquid. Next, push the plunger 30 again to dispense the injection liquid into a patient (see FIG. 3). The pushing will be stopped when the cone 311 inserts into a mated hollow (not numbered) in the rear extension 14 (see FIG. 4). Also, the connection member 31 is matingly secured to a conformed interior of the second coupling section 22. That is, the plunger 30, the second needle assembly 20, and the first needle assembly 10 are secured together. Next, clockwise rotate the plunger 30 about the syringe barrel 40 until the tabs 412 are stopped at bending points of the L-shaped grooves 23 (see FIGS. 5 and 6). At this position, a lengthwise movement of the plunger 30, the second needle assembly 20, and the first needle assembly 10 can be effected. Next, pull the plunger 30, the second needle assembly 20, and the first needle assembly 10 until being stopped. At this position, the breakable section 33 is about at the flange 44. Also, the needle 11 is retracted into the syringe barrel 40. Thus, a medical employee may break the breakable section 33 (see FIG. 7). Finally, the syringe can be safely thrown away.

Figure 8:
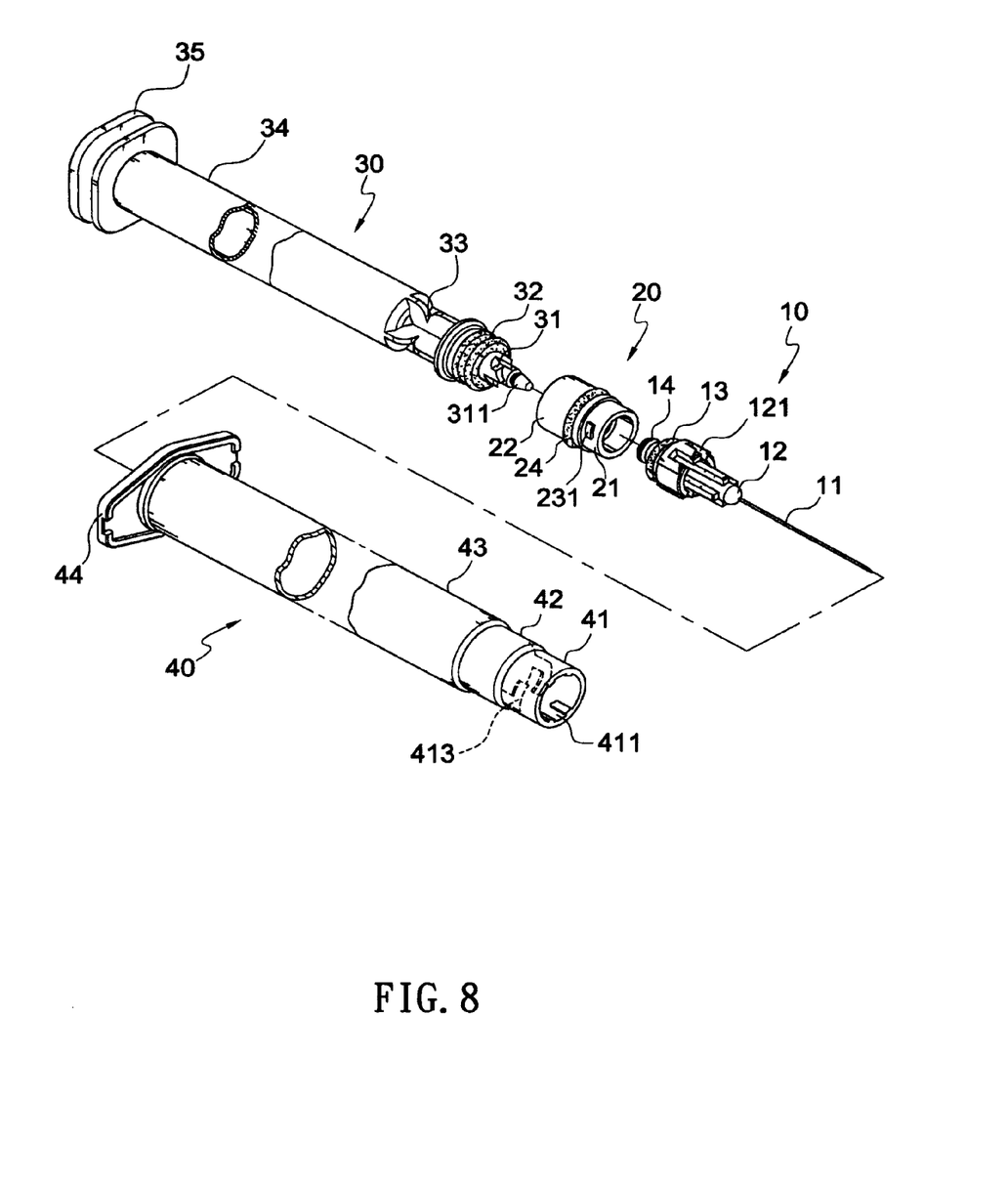
FIG. 8 is an exploded view of a second preferred embodiment of disposable safety syringe according to the invention.

Referring to FIG. 8, a disposable safety syringe in accordance with a second preferred embodiment of the invention is shown. The characteristics of the second preferred embodiment are detailed below. The tabs 231 (only one is shown) are formed on the outer surface of the first coupling section 21 and the L-shaped grooves 413 are formed on the inner surface of the first section 41.

Referring to FIGS. 9 to 15, a disposable safety syringe in accordance with a third preferred embodiment of the invention is shown. The characteristics of the third preferred embodiment are detailed below.

Figure 9:
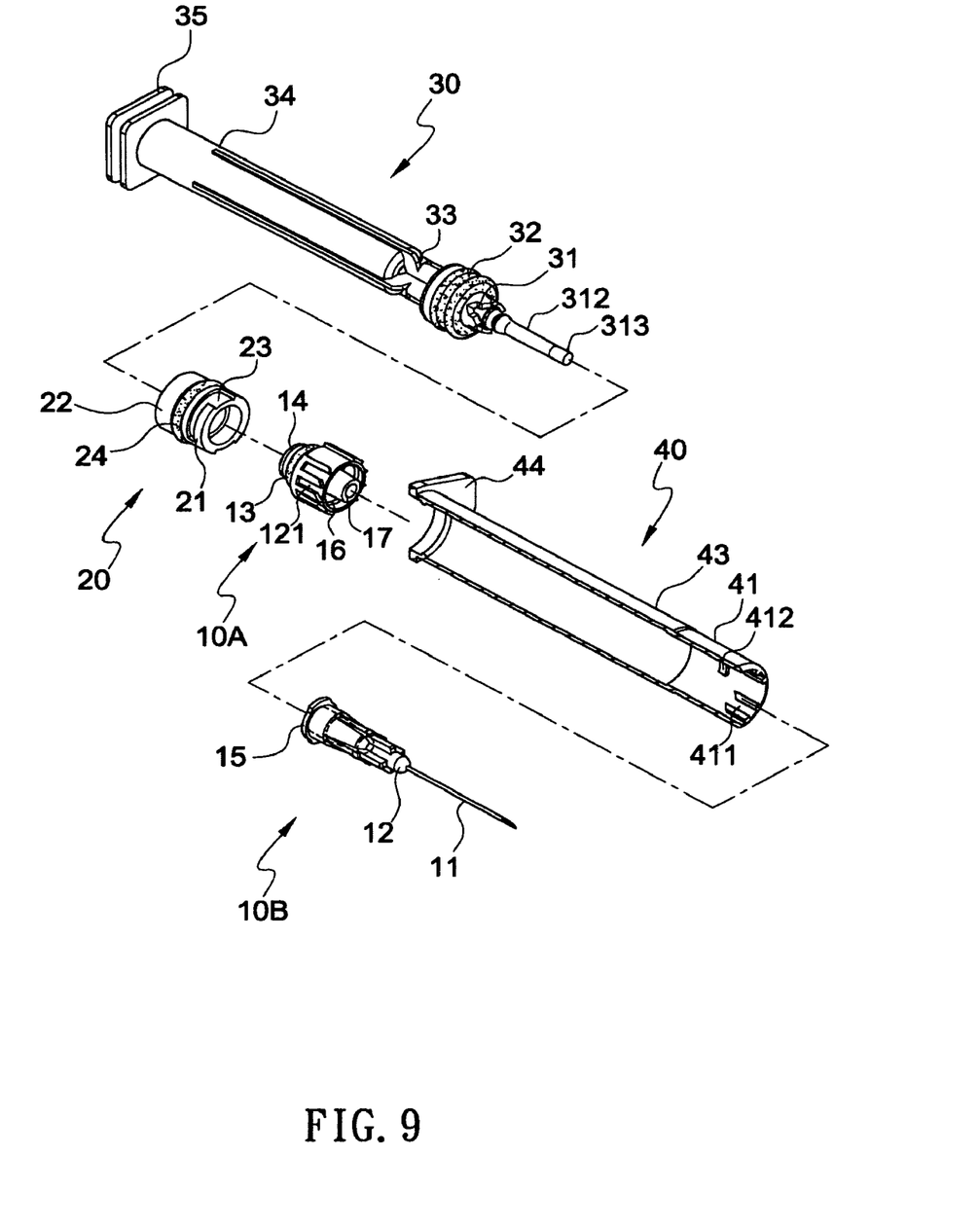
FIG. 9 is an exploded view in part section of a third preferred embodiment of disposable safety syringe according to the invention.
Figure 10:
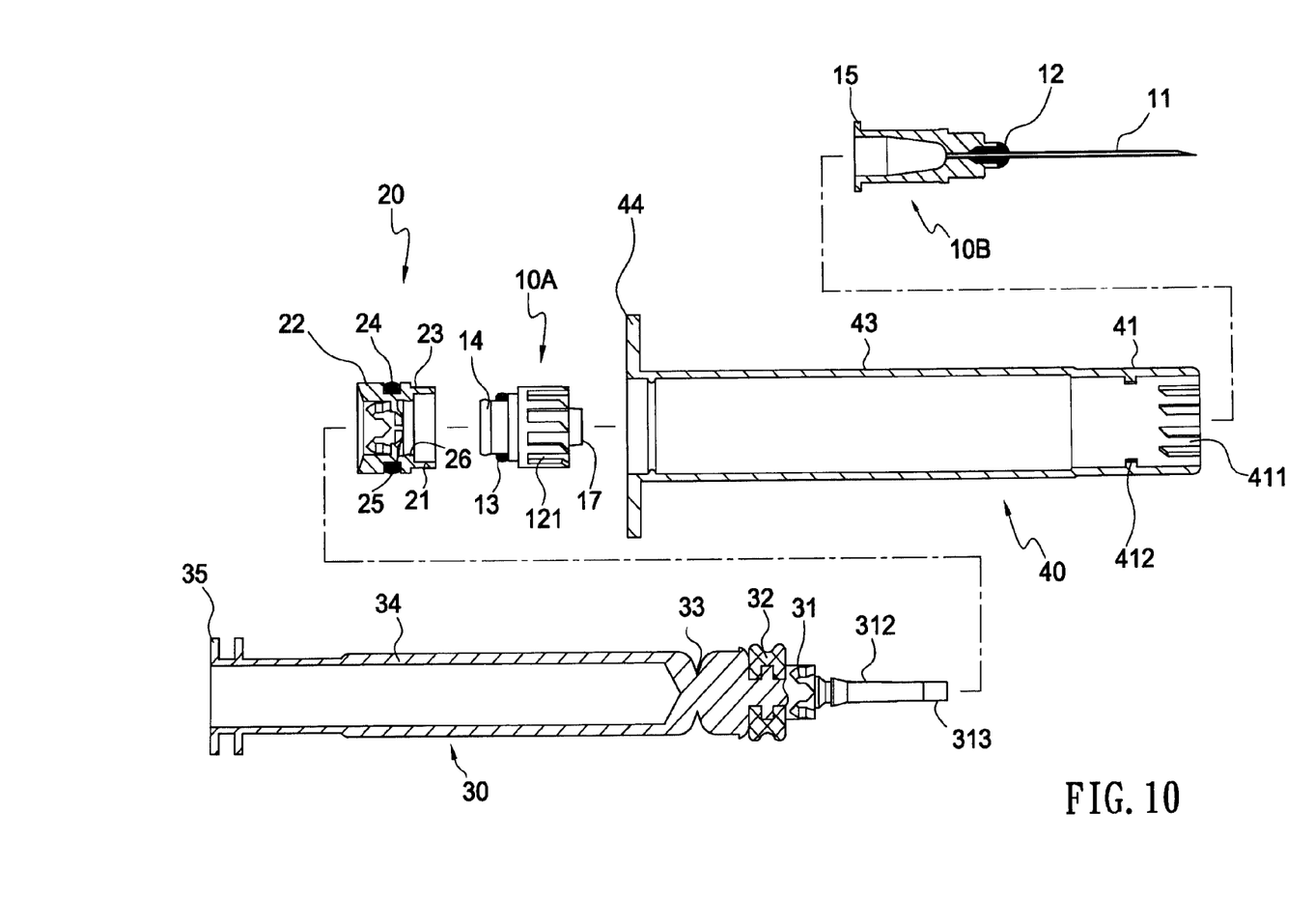
FIG. 10 is a longitudinal sectional view of the syringe of FIG. 9.

The first needle assembly 10 is comprised of rear and front portions 10A and 10B. The front portion 10B of the first needle assembly 10 comprises, from front to rear, a needle 11, a cylindrical needle seat 12, and a rear male thread 15. The rear portion 10A of the first needle assembly 10 comprises an internal thread 16, an axial hollow conic member 17 in communication with both ends, circumferential ridges 121 spaced therearound, a rear O-ring 13, and an extension 14 disposed rearward of the O-ring 13.

A second needle assembly 20 is a hollow cylindrical member with a central bore shaped to sealingly secure to both the first needle assembly 10 (i.e., O-ring 13 and extension 14) and the plunger 30 (i.e., connection member 31). The second needle assembly 20 comprises, from front to rear, a first coupling section 21 having two opposite L-shaped grooves 23 formed on an outer surface, an O-ring 24, and a second coupling section 22. Within the second needle assembly 20, there are further provided a stopping department 25 and an annular shoulder 26 between the stopping department 25 and a forward mouth thereof.

Figure 11:
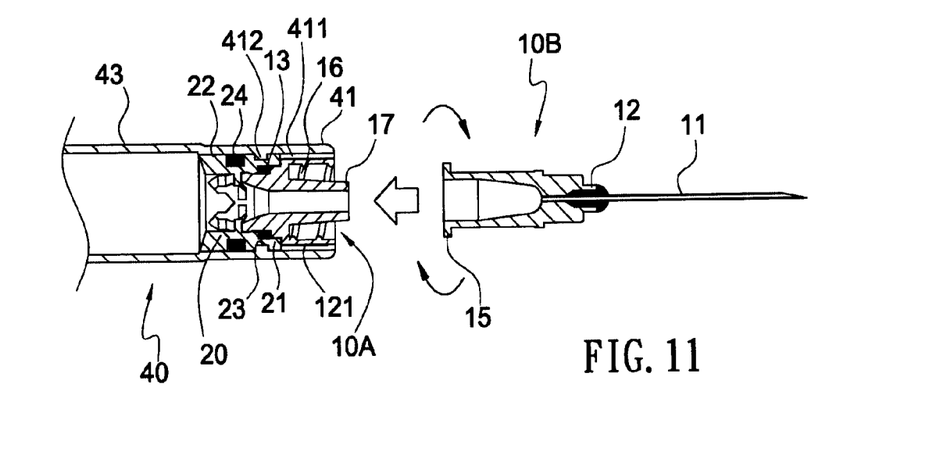
FIG. 11 is a longitudinal sectional view of the front portion of the assembled syringe of FIG. 9 showing the front portion of the first needle assembly to be assembled with the rear portion thereof.
Figure 12:
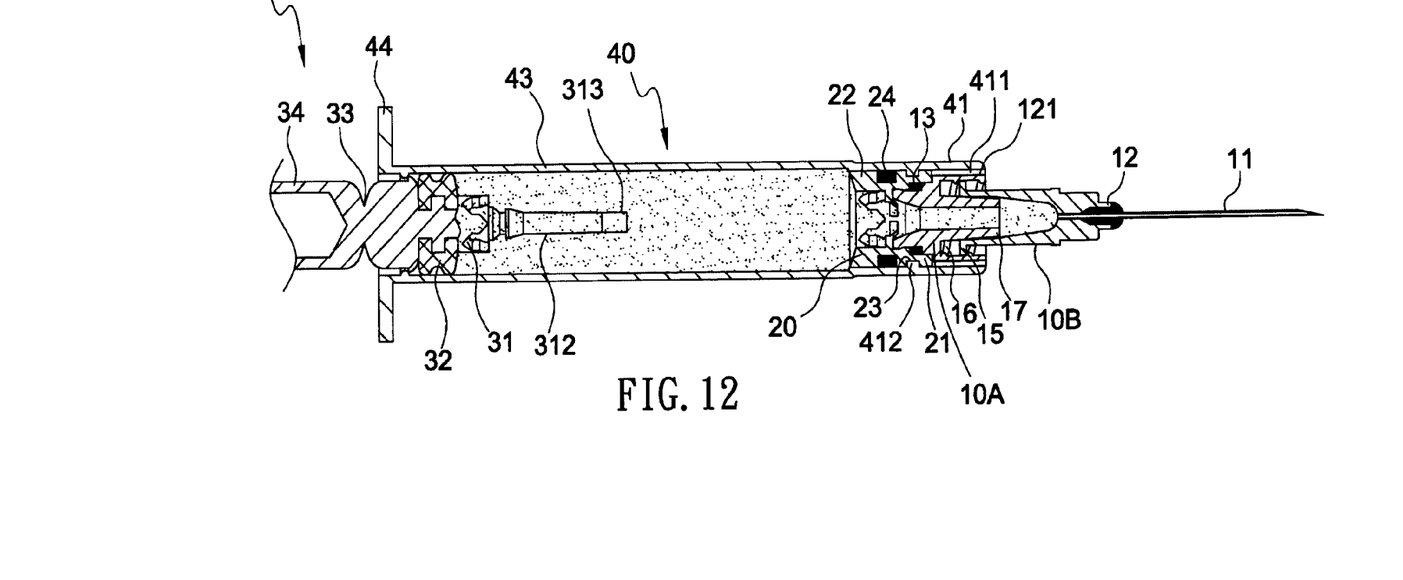
FIG. 12 is a longitudinal sectional view of the completely assembled syringe of FIG. 11 with injection liquid filled in the syringe barrel prior to dispensing.
Figure 13:
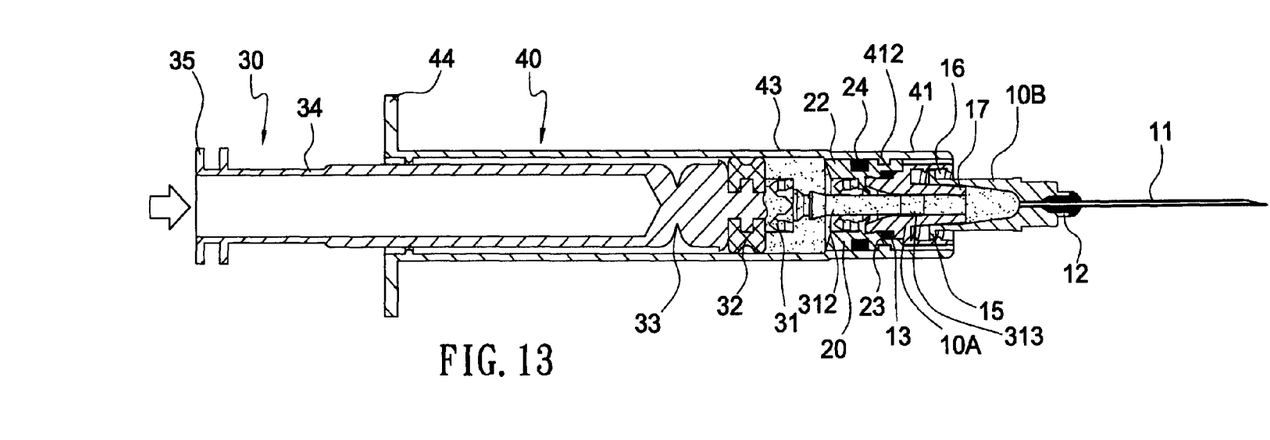
FIG. 13 is a view similar to FIG. 12 where the plunger is being pushed to dispense the injection liquid with the latches being gradually inserted into the first needle assembly.
Figure 14:
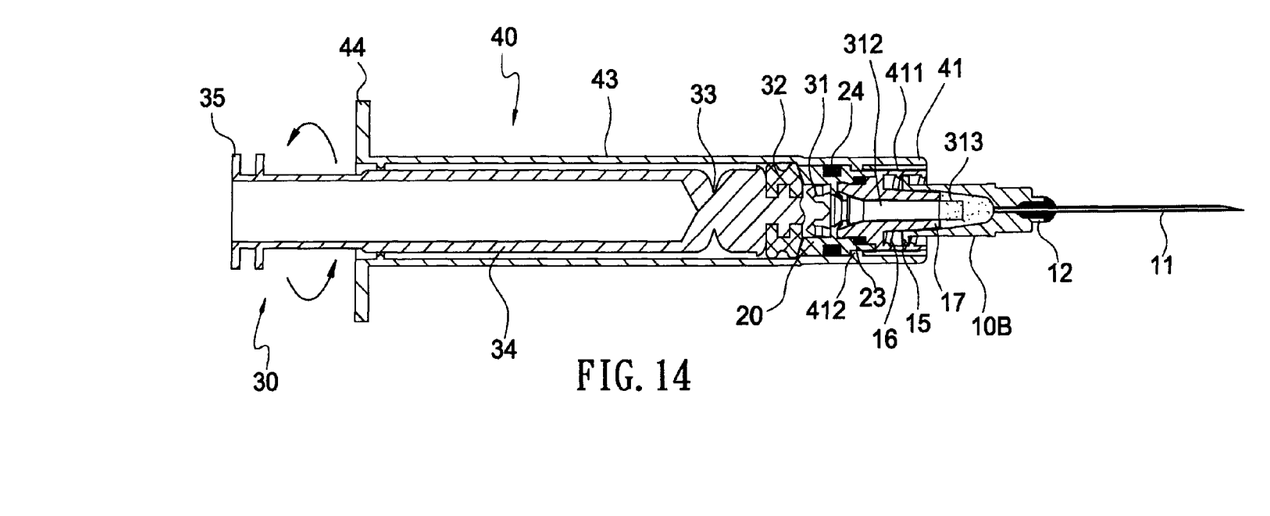
FIG. 14 is a view similar to FIG. 13 showing the plunger has rotated until bending points of the L-shaped grooves are stopped by the tabs so that a subsequent rearward movement of the plunger, the second needle assembly, and the first needle assembly can be effected.
Figure 15:
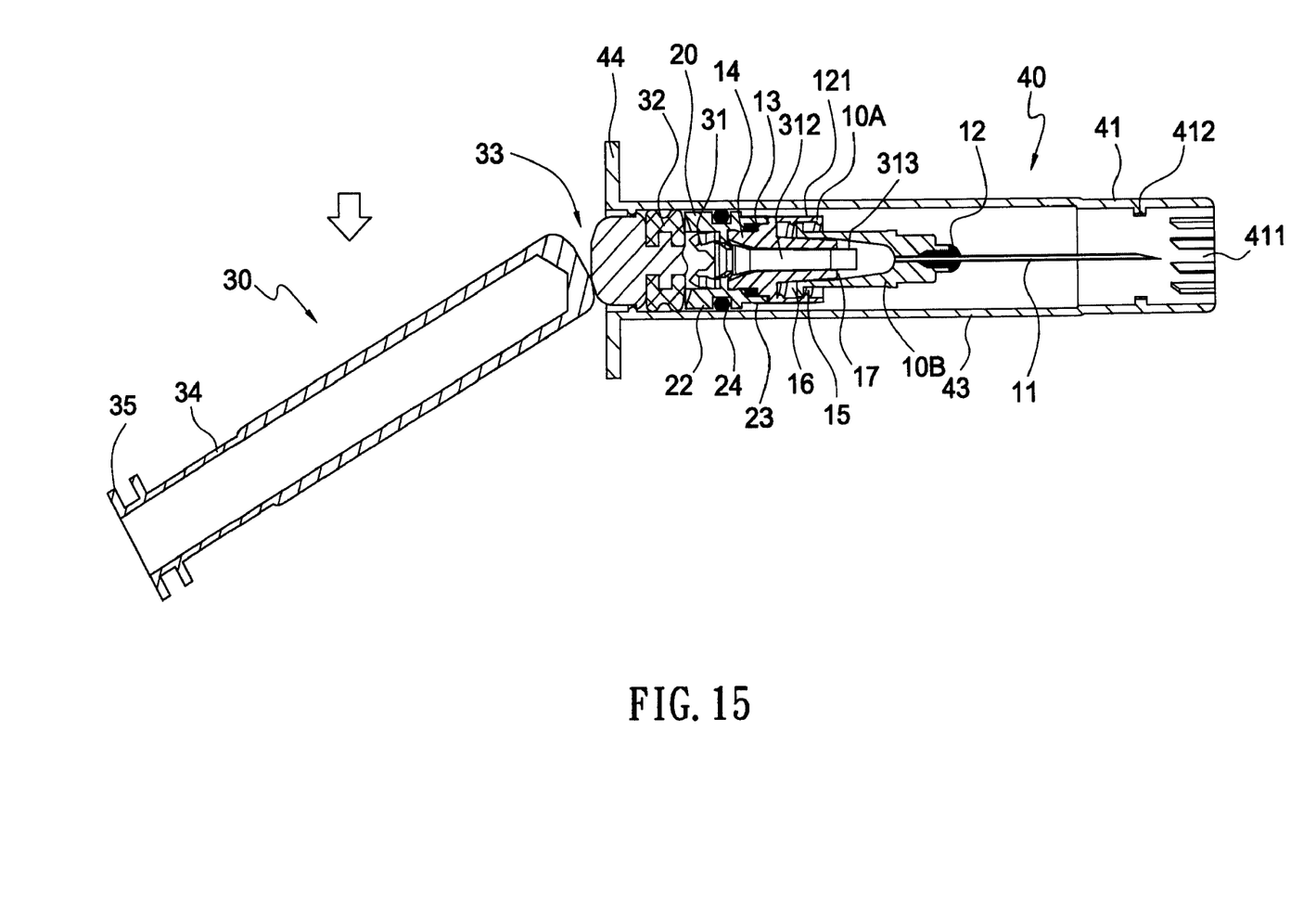
FIG. 15 is a view similar to FIG. 14 showing the breakable section of the plunger is broken by force after retracting the first needle assembly into the syringe barrel as a next step of FIG. 14.

The extension 14 is retained in the stopping department 25 and the O-ring 13 is sealingly engaged with the shoulder 26 when the rear portion 10A of the first needle assembly 10 and the second needle assembly 20 are assembled. The second needle assembly 20 has a portion lockingly fastened in the first section 41 by engaging the circumferential portions of the L-shaped grooves 23 with the tabs 412. The first needle assembly 10 is releasably fastened in the first section 41 with its rear extension 14 and O-ring 13 being tightly secured to the second needle assembly 20, the ridges 121 and the troughs 411 mating engaged each other, and the needle 11 exposed.

The male thread 15 may be rotated along the groove of the thread 16 until being stopped (i.e., a complete first needle assembly 10 is formed). The cone 311 of the plunger 30 is replaced with a forward extension 312 and a latches 313 formed on the behind end of the extension 312. The extension 312 is shaped to insert into the stopping department 25 when dispensing medical liquid.

In a liquid dispensing operation (see FIGS. 12 to 14), the plunger 30 is pushed to inject injection liquid into a patient until the latches 313 one-way limit the stopping department 25 into the hollow of the rear portion 10A of the first needle assembly 10 are secured together. Thereafter, clockwise rotate the plunger 30 about the syringe barrel 40 until the tabs 412 are stopped at bending points of the L-shaped grooves 23. At this position, a lengthwise movement of the plunger 30, the second needle assembly 20, and the first needle assembly 10 can be effected. Next, pull the plunger 30, the second needle assembly 20, and the first needle assembly 10 until being stopped. At this position, the breakable section 33 is about at the flange 44. Also, the needle 11 is retracted into the syringe barrel 40. Thus, a medical employee may break the breakable section 33 (see FIG. 15). Finally, the syringe can be safely thrown away.

Figure 16:
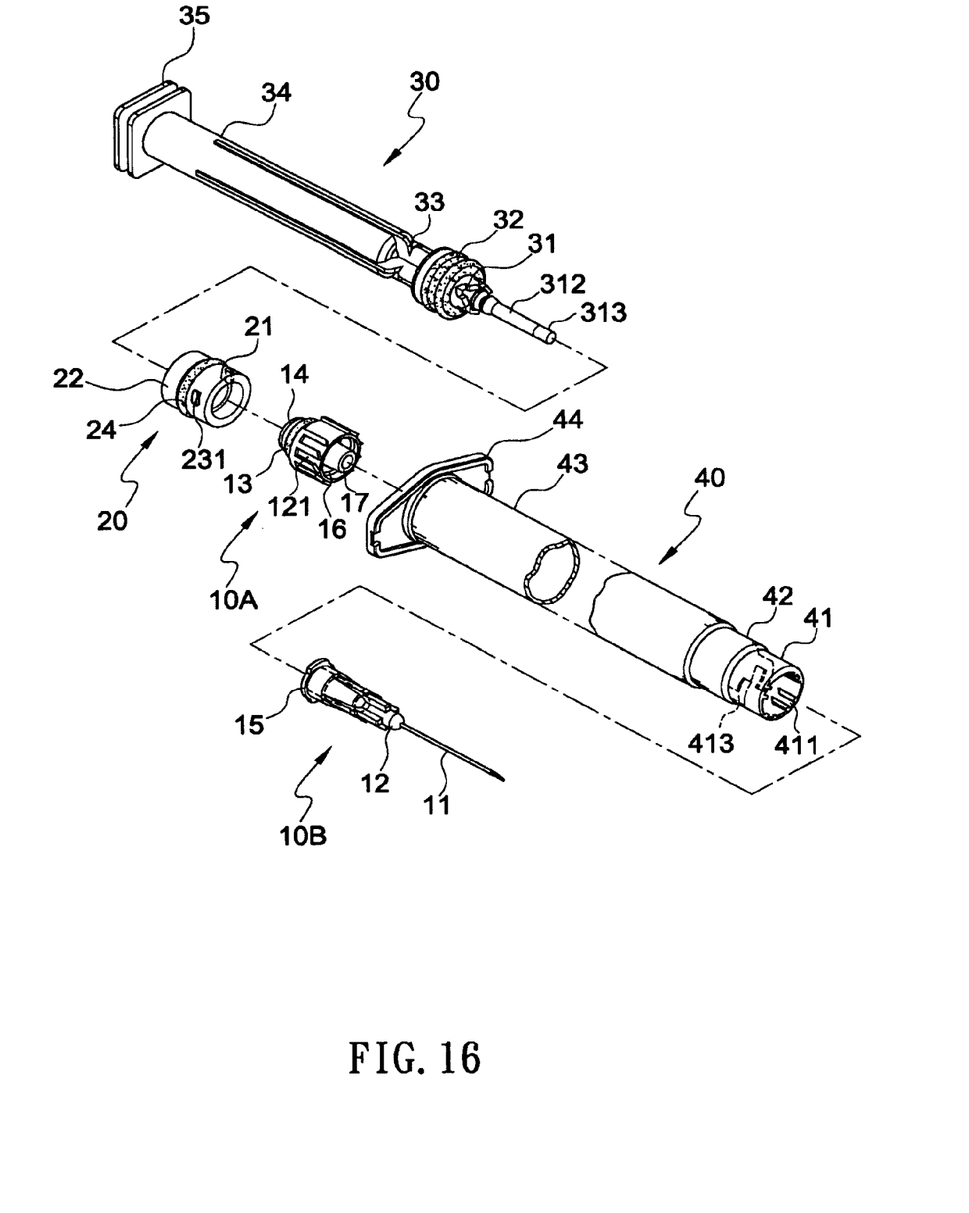
FIG. 16 is an exploded view of a fourth preferred embodiment of disposable safety syringe according to the invention.

Referring to FIG. 16, a disposable safety syringe in accordance with a fourth preferred embodiment of the invention is shown. The characteristics of the fourth preferred embodiment are detailed below. The tabs 231 are formed on the outer surface of the first coupling section 21 and the L-shaped grooves 413 are formed on the inner surface of the first section 41.

While the invention herein disclosed has been described by means of specific embodiments, numerous modifications and variations could be made thereto by those skilled in the art without departing from the scope and spirit of the invention set forth in the claims.

What is claimed is:

1. A disposable medical syringe comprising:
   a steeped syringe barrel comprising a proximal end, a distal end, a central bore, and two opposite mating members on an inner surface proximate the distal end;
   a plunger being reciprocable within the central bore of the syringe barrel and comprising a connection member with a protruding cone and a breakable section behind the connection member;
   a first needle assembly comprising a needle disposed at one end, an extension disposed at the other end and including a holding space, and at least two ridges secured to the distal end of the syringe barrel; and
   a hollow second needle assembly shaped to lockingly secure to the first needle assembly in the syringe barrel, the second needle assembly comprising a first coupling section disposed at one end for covering the extension of the first needle assembly, a second coupling section disposed inside the other end, and two opposite corresponding mating members on an outer surface, the corresponding mating members being lockingly engaged with the mating members, the connection member of the plunger inserting in the second needle assembly and engaging with the second coupling section of the second needle assembly, the cone of the connection member fully coupling in the first coupling section of the first needle assembly;
   wherein the plunger may push to dispense injection liquid filled in the syringe barrel until the connection member is stopped by both the second needle assembly and the first needle assembly with the plunger, the second needle assembly, and the first needle assembly being secured together;
   wherein the plunger may clockwise rotate about the syringe barrel until the mating members and the corresponding mating members are unlocked lengthwise each other; and
   wherein the plunger, the second needle assembly, and the first needle assembly may move rearward to retract the needle within the syringe barrel until being stopped with the breakable section being disposed at the proximal end of the syringe barrel.

2. The disposable medical syringe of claim 1, wherein the mating members are tabs and the corresponding mating members are L-shaped grooves.

3. The disposable medical syringe of claim 1, wherein the mating members are L-shaped grooves and the corresponding mating members are tabs.

* * * * *